United States Patent [19]

Petranek et al.

[11] 4,379,041
[45] Apr. 5, 1983

[54] POLYMERIC MEMBRANE SELECTIVE TO CALCIUM (II) IONS

[75] Inventors: Jaroslav Petránek; Olen Ryba, both of Prague; Miloslav Semler; Miroslav Panoch, both of Turnov, all of Czechoslovakia

[73] Assignee: Ceskoslovenska akademie ved, Prague, Czechoslovakia

[21] Appl. No.: 250,019

[22] Filed: Apr. 1, 1981

[30] Foreign Application Priority Data

Apr. 24, 1980 [CS]  Czechoslovakia ................... 2865-80

[51] Int. Cl.³ ............................................. G01N 27/46
[52] U.S. Cl. ................................................... 204/415
[58] Field of Search ....................... 204/195 M, 195 L

[56] References Cited

U.S. PATENT DOCUMENTS

| | | | |
|---|---|---|---|
| 3,706,649 | 12/1972 | Cosgrove et al. | 204/195 M |
| 3,729,401 | 4/1973 | Cosgrove et al. | 204/195 L |
| 3,843,505 | 10/1974 | Higuchi . | |
| 3,932,233 | 1/1976 | Ruzicka et al. | 204/195 M |
| 3,957,607 | 4/1976 | Simon et al. | 204/195 M |
| 4,251,470 | 2/1981 | Owen et al. | 204/195 M |

OTHER PUBLICATIONS

Oehme et al., "Neutral Carrier Ca²⁺-Microelectrode", Chimia 30, (1976), No. 3, (Marz), pp. 204-206.

*Primary Examiner*—T. Tung
*Attorney, Agent, or Firm*—Murray Schaffer

[57] ABSTRACT

Polymeric membrane selective to calcium (II) ions. The invention relates to a polymeric membrane selective to calcium (II) ions, formed by a solid film of plastic material, advantageously of poly(vinyl chloride), which contains an active neutral carrier in a plasticizer of the used plastic material. The active carrier is a complex of macrocyclic polyetherdiamides of the general formula

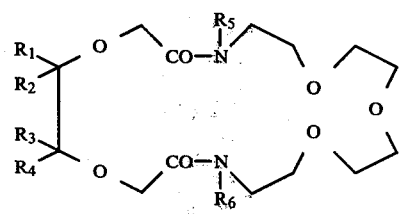

where $R_1$, $R_2$, $R_3$, $R_4$ are H or alkyl containing 1 to 4 carbon atoms, advantageously methyl, $R_5$ and $R_6$ mean alkyl or arylalkyl with 6 to 10 carbon atoms, advantageously benzyl, with the calcium (II) ions and a lipophilic organic anion, advantageously with tetraphenylborate or tetra(p-chlorophenyl)borate anion.

4 Claims, No Drawings

POLYMERIC MEMBRANE SELECTIVE TO CALCIUM (II) IONS

The invention pertains to polymeric membranes selective to calcium(II) ions.

Ion-selective electrodes for calcium, which are described in literature, employ various types of function membranes. In the first place, they are solid membranes from inorganic crystals, as $CaF_2 + LaF_3$ (Farren, G. M., Ger. 2,101,339) or $CaWO_4$ (Veselý, J.; Jindra, J., Czech.163,358), and poly(vinyl chloride) membranes, which contain calcium (II) salt of octyl-phenylphosphoric acid (Tjell, J. C.; Růžička, J., Ger. Offen. 2 349 299) or of (1,1,3,3-tetramethylbutyl)phenylphosphoric acid (Cosgrove, R. E., U.S. Pat. No. 3,729,401) as an active component. The sensors based on single crystals did not find broader application, above all, because of their low selectivity and nonideal responses. A serious disadvantage of the electrodes based on calcium (II) alkylphosphates is a considerable dependence of the response on pH, which complicates their analytical utilization. The shortcomings of both types of above mentioned membranes are overcome in membranes with neutral carriers. A number of noncyclic neutral ionophores for the membranes selective to calcium were described by Simon et al. (Helv. Chim. Acta 58, 1535 (1975). Certain disadvantage of the sensors based on these neutral carriers consists in memory effects of the membranes, which make the response worse on passing from the more concentrated solutions to the more diluted ones.

The objective of the invention is a membrane selective to calcium(II) ions, which is formed by a solid film of plastic material, advantageously of poly(vinyl chloride), containing an active neutral carrier in a plasticizer of the above plastic material. The active neutral carrier according to the invention is a complex of macrocyclic polyetherdiamides of the general formula I

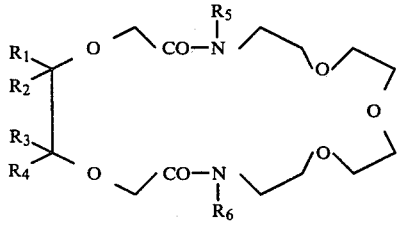

where $R_1$, $R_2$, $R_3$, $R_4$ are H or alkyl containing 1–4 carbon atoms, preferably methyl, $R_5$ and $R_6$ mean alkyl or arylalkyl with 6–10 carbon atoms, preferably benzyl, while the general composition of the complex with calcium(II) ion and a lipophilic organic anion, advantageously tetraphenylborate or tetra(p-chlorophenyl)borate anion, is

where $A^-$ is a lipophilic organic anion.

Macrocyclic polyetherdiamides are prepared by the reaction of dichlorides of the correspondingly substituted 3,6-dioxa-octane-1,8-dicarboxylic acids with N,N'-dibenzyl-1,11-diamino-3,6,9-trioxaundecane by the earlier described method (Petránek, J.; Ryba, O., Collect.Czech.Chem.Commun. 45, 1567 (1980)).

As suitable plasticizers, they may be advantageously used plasticizers with the dielectric constants higher than 10, for example, nitrated alkylarylethers, preferably nitrated phenyl-n-alkylethers, where alkyl contains more than 6 carbon atoms in the chain.

The advantage of calcium selective electrodes, based on the above given complex, consists in the precisely defined composition of active component and in a linear response with a theoretical course over the broad concentration range of $10^{-1}$ M to $10^{-5}$ M $Ca^{2+}$. The response of electrode to the activity of calcium(II) ions is virtually instantaneous without memory effects. The electrodes exhibit a high selectivity to calcium(II) ions, namely with respect to ions of Na, Mg, K, Rb and Cs.

The invention is further illustrated in examples of performance without limiting its scope by any means.

EXAMPLE 1

The solution of 0,5 g of potassium tetra(p-chlorophenyl) borate in 3 cm³ of methanol was added to the solution of 0,55 g of polyetherdiamide of formula I ($R_1$, $R_2$, $R_3$, $R_4 = CH_3$; $R_5$, $R_6 =$ benzyl) and 0,07 g $Ca(SCN)_2$ in 5 ml of methanol. The separating white precipitate was isolated by filtration, crystalized from nitromethane and dried at 110° C. The yield was 0,7 g of the complex; m.p. 218°–220° C. The composition was according to elemental analysis 2 $C_{32}H_{46}N_2O_7.Ca.2(ClC_6H_4)_4B$.

EXAMPLE 2

The complex of elemental composition 2 $C_{31}H_{44}N_2O_7.Ca.2(ClC_6H_4)_4B$ and m.p. 238°–241° C. was obtained by the same procedure as in Example 1 from the solution of polyetherdiamide I ($R_1 = R_2 = R_3 = CH_3$; $R_4 = H$; $R_5 = R_6 =$ benzyl).

EXAMPLE 3

The complex of elemental composition 2 $C_{30}H_{42}N_2O_7.Ca.2(ClC_6H_4)_4B$ and m.p. 104°–106° C. was obtained by the same method as in Example 1 (except the drying temperature, which was 80° C.) from the solution of polyetherdiamide I ($R_1 = R_3 = CH_3$; $R_2 = R_4 = H$; $R_5 = R_6 =$ benzyl).

EXAMPLE 4

The complex of elemental composition 2 $C_{28}H_{38}N_2O_7.Ca.2(ClC_6H_4)_4B$ and m.p. 95°–97° C. was prepared by the same procedure as described in Example 3 from the solution of polyetherdiamide I ($R_1 = R_2 = R_3 = R_4 = H$; $R_5 = R_6 =$ benzyl).

EXAMPLE 5

The solution of 0,35 g of sodium tetraphenylborate in 3 cm³ methanol was added to the solution of 0,55 g of polyetherdiamide I ($R_1 = R_2 = R_3 = R_4 = CH_3$; $R_5 = R_6 =$ benzyl) and 0,07 g of $Ca(SCN)_2$ in 5 cm³ of methanol. The separating white precipitate was filtered, crystallized from a mixture of nitromethane and ethyl acetate, and dried at 110° C. The complex of elemental composition 2 $C_{32}H_{46}N_2O_7.Ca.2(C_6H_5)_4B$ and m.p. 241°–243° C. was obtained in the yield of 0,65 g.

EXAMPLE 6

The complex prepared in Example 1 (50 mg) was dissolved in 1 cm³ of (o-nitrophenyl)octylether and mixed with 10 cm³ of the 5% solution of high-molecular-weight poly(vinyl chloride) in cyclohexanone. The solution was cast on a horizontal glass plate 7×15 cm. Cyclohexanone was evaporated at ambient temperature and a foil of thickness about 0,15 mm was obtained. A ring cut from the foil was fixed in an electrode body. The electrode was filled with an internal standard solution and assembled by insertion of a silver-silver chloride electrode. The following selectivity coefficients log $k_{CaM}$ were measured with the electrode prepared in this way for the ions M: Mg=−3,77; Sr=−0,93; Ba=−2.10; Li=−2.44; Na=−3,73; K=−3,66; Rb=−4,09; Cs=−4,30.

EXAMPLE 7

The membrane and electrode were prepared from the complex according to Example 2 by the same procedure as described in Example 6. The following selectivity coefficients log $k_{CaM}$ were determined with the calcium-selective electrode for the ions M: Mg=−3,63; Sr=−0,71; Ba=−1.28; Li=−2,21; Na=−2,94; K=−2,84, Rb=−2,84; Cs=−2,68.

EXAMPLE 8

The electrode was made by the procedure described in Example 6 from the complex according to Example 3. The following selectivity coefficients log $k_{CaM}$ were measured for the ions M: Mg=−3,11; Sr=−0,69; Ba=−1,01; Li=−2,82; Na=−3,36; K=−3,07; Rb=−3,07; Cs=−2,77.

EXAMPLE 9

The calcium-selective electrode was prepared by the method described in Example 6 from the complex according to Example 4 and showed the following selectivity coefficients log $k_{CaM}$ for the ions M: Mg=−3,27; Sr=−1,82; Ba=−2,82; Li=−2,48; Na=−2,76; K=−2,21; Rb=−2,25; Cs=−1,76.

EXAMPLE 10

The calcium-selective electrode was prepared from the complex according to Example 1 in the same way as in Example 6, with the distinction that (2,4-dinitrophenyl)octylether was used instead of (o-nitrophenyl)octylether. The following selectivity coefficients log $k_{CaM}$ were obtained with this electrode for the ions M: Mg=−3,78; Sr=−0,85; Ba=−1,86; Li=−2,20; Na=−3,14; K=−3,32; Rb=−3,32; Cs=−3,27.

EXAMPLE 11

The calcium-selective electrode wad made from the complex according to Example 1 by the same method as in Example 6, with the distinction that (o-nitrophenyl)-n-decylether was used instead of (o-nitrophenyl)octylether. The following selectivity coefficients log $k_{CaM}$ were measured with this electrode for the ions M: Mg=−3,64; Sr=−0,78; Ba=−1,76; Li=−1,91; Na=−3,33; K=−3,32; Rb=−3,42; Cs=−3,38.

We claim:

1. A membrane selective to calcium (II) ions, formed by a solid film of plastic material which contains an active neutral carrier in a plasticizer for the plastic material, wherein the active carrier is a ternary complex of (a) a macrocyclic polyetherdiamide of the general formula

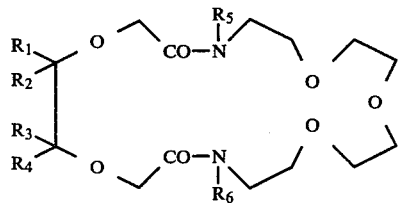

where $R_1$, $R_2$, $R_3$, $R_4$ are H or alkyl containing 1 to 4 carbon atoms, $R_5$ and $R_6$ are alkyl or arylalkyl with 6 to 10 carbon atoms with (b) the calcium (II) ion and (c) a lipophilic organic anion, while the general formula of the ternary complex is $$2\ \text{polyetherdiamide} \cdot \text{Ca} \cdot 2\text{A}^-,$$

where $A^-$ is the lipophilic organic anion.

2. A membrane as claimed in claim 1, wherein the plastic material is polyvinyl chloride.

3. A membrane as claimed in claim 1, wherein $R_1$, $R_2$, $R_3$, $R_4$ are methyl.

4. A membrane as claimed in claim 1, wherein the lipophilic organic anion is selected from the group consisting of tetraphenylborate and tetra(p-chlorophenyl) borate anions.

* * * * *